United States Patent [19]

Sallmann et al.

[11] 4,421,765
[45] Dec. 20, 1983

[54] SUBSTITUTED PHENYLACETIC ACID AMIDE COMPOUNDS

[75] Inventors: Alfred Sallmann, Bottmingen; Gerhard Baschang, Bettingen, both of Switzerland

[73] Assignee: Ciba-Geigy Corporation, Ardsley, N.Y.

[21] Appl. No.: 193,776

[22] Filed: Oct. 3, 1980

Related U.S. Application Data

[60] Division of Ser. No. 33,295, Apr. 25, 1979, Pat. No. 4,250,192, which is a continuation of Ser. No. 905,087, May 11, 1978, abandoned, and Ser. No. 906,292, May 15, 1978, abandoned.

[30] Foreign Application Priority Data

May 11, 1977 [LU] Luxembourg ................... 77316
Sep. 9, 1977 [LU] Luxembourg ................... 78106

[51] Int. Cl.$^3$ ................... A61K 31/24; C07C 101/44
[52] U.S. Cl. ................... 424/309; 560/39; 560/41; 560/38; 562/448; 562/449; 562/450; 424/319
[58] Field of Search ............ 424/309, 319; 560/38, 560/39, 41; 562/448, 449, 450

[56] References Cited

U.S. PATENT DOCUMENTS

| | | | |
|---|---|---|---|
| 3,536,758 | 10/1970 | Sallmann et al. | 424/319 |
| 3,652,762 | 3/1972 | Sallmann | 560/41 |
| 3,897,782 | 7/1975 | Baltze et al. | 562/449 |

*Primary Examiner*—James H. Reamer
*Attorney, Agent, or Firm*—Michael W. Glynn

[57] ABSTRACT

Phenylacetic acid amide compounds of the formula

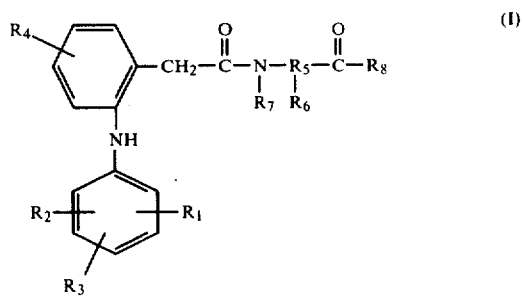

in which $R_1$ is hydrogen, lower alkyl, lower alkoxy, halogen having an atomic number of not more than 35 or trifluoromethyl, $R_2$ is hydrogen, lower alkyl, lower alkoxy, halogen having an atomic number of not more than 35 or trifluoromethyl, $R_3$ is hydrogen, lower alkyl, lower alkoxy or halogen having an atomic number of not more than 35 and $R_4$ is hydrogen, lower alkyl, lower alkoxy or halogen having an atomic number of not more than 35, and in which $R_5$ is a radical of aliphatic character containing the group $R_6$, $R_6$ and $R_7$ are each hydrogen or together are a divalent aliphatic radical and the group of the formula $-C(=O)-R_8$ (Ia) is a carboxyl group, which can be functionally modified, and their salts are useful as anti-inflammatory agents.

10 Claims, No Drawings

SUBSTITUTED PHENYLACETIC ACID AMIDE COMPOUNDS

CROSS REFERENCE

This is a divisional of application Ser. No. 033,295, filed on Apr. 25, 1979 now U.S. Pat. No. 4,250,192, which is a continuation of our copending applications Ser. No. 905,087, filed May 11, 1978, now abandoned, and Ser. No. 906,292, filed May 15, 1978, now abandoned.

The invention relates to novel substituted phenylacetic acid amide compounds and also to processes for their preparation and to pharmaceutical formulations which contain these novel compounds and also to the use thereof.

The invention relates in particular to novel phenylacetic acid amide compounds of the formula

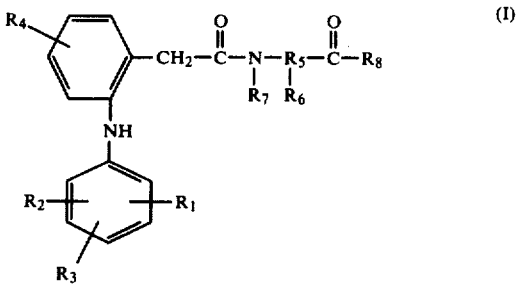

in which $R_1$ is hydrogen, lower alkyl, lower alkoxy, halogen having an atomic number of not more than 35 or trifluoromethyl, $R_2$ is hydrogen, lower alkyl, lower alkoxy, halogen having an atomic number of not more than 35 or trifluoromethyl, $R_3$ is hydrogen, lower alkyl, lower alkoxy or halogen having an atomic number of not more than 35 and $R_4$ is hydrogen, lower alkyl, lower alkoxy or halogen having an atomic number of not more than 35, and in which $R_5$ is a radical of aliphatic character containing the group $R_6$, $R_6$ and $R_7$ are each hydrogen or together are a divalent aliphatic radical and the group of the formula $—C(=O)—R_8$ (Ia) is a carboxyl group, which can be functionally modified, and also salts of such compounds having salt-forming properties.

The radicals and compounds qualified by the term "lower" in this specification contain not more than 7 and in particular not more than 4 carbon atoms.

In the radical $R_5$ of aliphatic character in a compound of the formula I, the amino group of the formula —NH— and the carboxyl group of the formula $—C(=O)—R_8$ (Ia), which can be functionally modified, and also the group $R_6$ are bonded to carbon atoms of aliphatic character in the radical $R_5$.

The radical of the formula $—R_5(R_6)—$ (Ib) is in particular substituted or unsubstituted lower alkylene or, preferably, substituted or unsubstituted lower alkylidene. Substituents of a radical of this type are functional groups, such as free or etherified hydroxyl or mercapto, a S'-substituted dithio group, carboxyl, which can be functionally modified, or substituted or unsubstituted amino and/or aromatic or heterocyclic radicals.

Etherified hydroxyl is preferably lower alkoxy, whilst etherified mercapto is especially lower alkylthio.

The second sulphur atom of a S'-substituted dithio group preferably contains, as the substituent, the radical of a compound of the formula I, which is bonded via the grouping of the formula $—R_5(R_6)—$ (Ib).

Functionally modified carboxyl, as a substituent of $—R_5(R_6)—$ (Ib), is, for example, esterified carboxyl, especially lower alkoxycarbonyl and also phenyl-lower alkoxycarbonyl or carbamoyl.

Substituted amino is, for example, guanidino, lower alkylamino or di-lower alkylamino.

An aromatic radical, as a substituent of a grouping of the formula $—R_5(R_6)—$ (Ib), is substituted or unsubstituted phenyl, substituents being, for example, lower alkyl, hydroxyl, lower alkoxy and/or halogen.

A heterocyclic radical, as a substituent of lower alkylene or lower alkylidene of the formula $—R_5(R_6)—$ (Ib), is in particular a monocyclic or bicyclic, monoazacyclic or diazacyclic radical of aromatic character which is bonded via a carbon atom of the azacyclic ring to the radical of the formula $—R_5(R_6)—$ (Ib), especially imidazolyl, for example 4-imidazolyl, or indolyl, for example 3-indolyl.

A divalent aliphatic radical formed by the groups $R_6$ and $R_7$ together is, in particular, lower alkylene which is unsubstituted or substituted, for example by free, etherified or esterified hydroxyl; i.e., together with $R_7$ and the nitrogen atom containing this group, the grouping of the formula $—R_5(R_6)—$ (Ib) can be an azacycloalkylene which is bonded via the nitrogen atom and a carbon atom and is unsubstituted or substituted, for example as indicated.

A functionally modified carboxyl group of the formula $—C(=O)—R_8$ (Ia) is, for example, an esterified carboxyl group, especially lower alkoxycarbonyl and also phenyl-lower alkoxycarbonyl, or an amidated carboxyl group, such as aminocarbonyl which is unsubstituted or N-monosubstituted or N,N-disubstituted by lower alkyl, or a group of the formula $—C(=O)—N(-R_7{}^a)—R_5{}^a(R_6{}^a)—C(=O)—R_8{}^a$ (Ic), in which $R_5{}^a$, $R_6{}^a$, $R_7{}^a$ and $R_8{}^a$ have the meaning defined for the radicals $R_5$, $R_6$, $R_7$ and $R_8$ respectively but do not need to be identical to these radicals.

The radical of the formula $—N(R_7)—R_5(R_6)—C(O=)—R_8$ (Id) is that of an aminoacid compound or a peptide compound of the formula

and in particular of a corresponding α-aminoacid compound, such as of the acid itself or of an ester or amide thereof, or of a peptide composed of corresponding α-aminoacid compounds, such as a dipeptide or tripeptide. In this case, the bond to the 2-diphenylamineacetic acid moiety of the compound of the formula I is preferably via the α-amino group of an α-aminoacid, but can also be via an amino group which may additionally be present. Preferred radicals of aminoacid compounds of the formula II or of aminoacids which are suitable for forming a peptide compound of the formula II are radicals of those aminoacids for which the information for protein biosynthesis is available in the genetic code, i.e. of aminoacids which are present in naturally occurring peptide or protein substances, and such aminoacids can be in the DL-form or also in the D- or L-form, and preferably at least the aminoacid which corresponds to the radical of the formula —N(R$_7$)—R$_5$(R$_6$)—C(=O)— has the D-configuration.

In the preceding the following text, the general terms can have the following meaning:

Lower alkyl is, for example, methyl, ethyl, n-propyl, isopropyl, n-butyl, isobutyl, sec.-butyl or tert.-butyl, and also n-pentyl, n-hexyl, isohexyl or n-heptyl.

Lower alkoxy is, for example, methoxy, ethoxy, n-propoxy, isopropoxy or n-butoxy.

Halogen is fluorine or bromine, but preferably chlorine.

Lower alkylene of the formula —R$_5$(R$_6$)— (Ib), in which R$_6$ is hydrogen, is, for example, ethylene, 1,2- or 1,3-propylene or 1,4-butylene, whilst corresponding lower alkylidene is, for example, methylene, ethylidene, n-propylidene, isopropylidene, n-butylidene, isobutylidene, 2-methyl-n-butylidene or isopentylidene.

Lower alkylthio is especially methylthio and also ethylthio.

Lower alkoxycarbonyl is, for example, methoxycarbonyl or ethoxycarbonyl, and also n-propoxycarbonyl or isopropoxycarbonyl.

Lower alkylamino is, for example, methylamino or ethylamino, whilst di-lower alkylamino is, for example, dimethylamino or diethylamino.

Amongst the substituted lower alkylene radicals and especially the substituted lower alkylidene radicals of the formula —R$_5$(R$_6$)— (Ib), in which R$_6$ is hydrogen, preferred radicals are: hydroxy-lower alkylidene, in particular 2-hydroxyethylidene or 2-hydroxypropylidene, mercapto- or lower alkylthio-lower alkylidene, preferably 2-mercaptoethylidene or 3-methylthiopropylidene, carboxy-lower alkylidene, in particular 2-carboxyethylidene or 3-carboxypropylidene, carbamoyl-lower alkylidene, especially 2-carbamoylethylidene or 3-carbamoylpropylidene, amino-lower alkylidene, preferably 3-aminopropylidene or 5-aminopentylidene, guanidino-lower alkylidene, in particular 4-guanidinobutylidene, phenyl-lower alkylidene which can be substituted in the phenyl radical by hydroxyl, especially 2-phenylethylidene or 2-(4-hydroxyphenyl)-ethylidene, imidazolyl-lower alkylidene, in particular 2-(4-imidazolyl)-ethylidene, and indolyl-lower alkylidene, preferably 2-(3-indolyl)-ethylidene, and also phenyl-lower alkylene, for example 1-phenylethylene.

If, in a group of the formula —R$_5$(R$_6$)— (Ib), the radical R$_6$ differs from hydrogen and, in a compound of the formula I, together with the group R$_7$ is a divalent aliphatic radical, the groups R$_5$, R$_6$ and R$_7$ together with the nitrogen atom then preferably form a 1,2-pyrrolidinylene radical, i.e. in such a case, R$_5$ is preferably methylene and the groups R$_6$ and R$_7$ together form 1,3-propylene.

N-lower alkyl- and N,N-di-lower alkyl-carbamoyl are, for example, methylcarbamoyl, ethylcarbamoyl or dimethylcarbamoyl.

The compounds of the formula I which have salt-forming properties can be in the free form or in the form of their salts, especially their pharmaceutically acceptable non-toxic salts. Compounds of the formula I containing acid salt-forming groups, especially containing free carboxyl groups, can form salts with bases, such as alkali metal salts or alkaline earth metal salts, especially sodium salts, potassium salts, magnesium salts or calcium salts, and also ammonium salts, as well as salts with organic bases, such as with suitable amines, for example ethylamine, triethylamine, ethanolamine, diethanolamine, diethylaminoethanol, ethylenediamine, benzylamine, procaine, pyrrolidine, piperidine, morpholine, 1-ethyl-piperidine or 2-piperidinoethanol. Compounds of the formula I containing basic salt-forming groups, especially containing amino and guanidino groups, can form acid addition salts, inter alia with inorganic acids, such as hydrogen halide acids, for example hydrochloric acid or hydrobromic acid, or sulphuric acid or phosphoric acid, or with organic acids, such as aliphatic, cycloaliphatic, aromatic or heterocyclic carboxylic or sulphonic acids, for example formic acid, acetic acid, propionic acid, succinic acid, glycollic acid, lactic acid, malic acid, tartaric acid, citric acid, ascorbic acid, maleic acid, hydroxymaleic acid, fumaric acid, 4-hydroxybenzoic acid, salicyclic acid, 4-aminosalicyclic acid, embonic acid, methanesulfonic acid, ethanesulphonic acid, 2-hydroxyethanesulphonic acid, ethylenesulphonic acid or toluenesulphonic acid. Compounds of the formula I which contain an acid salt-forming group and a basic salt-forming group can also be in the form of the inner salts.

The novel compounds of the present invention can be in the form of mixtures of isomers, such as racemates, or of pure isomers, for example antipodes.

The compounds according to the invention have valuable pharmacological properties, especially anti-inflammatory and analgesic properties. The anti-inflammatory activity can be demonstrated, for example, in rats with the aid of the distinct action in the kaolin paw oedema test according to Helv. Physiol. Acta 25, 156 (1967) when administered perorally in the dosage range of about 1 to 10 mg/kg and with the aid of the distinct action in the adjuvant arthritis model according to Pharmacology 2, 288 (1969) when administered perorally in the dosage range of about 10 to 30 mg/kg and also in vitro with the aid of the inhibitory action on the synthetic of prostaglandins from arachidonic acid by bovine spermatocystic enzymes in the concentration range of about 50 to 200 mg/l. The analgesic action manifests itself, for example, in the writhing syndrome in mice according to Pharmacol. exp. Therap. 125, 237 (1959) when administered perorally in the dosage range of about 100 mg/kg.

It has also been found that the novel compounds of the formula I, especially those in which at least the aminoacid corresponding to the radical of the formula —N(R$_7$)—R$_5$(R$_6$)—C(=O)— has the D-configuration, are distinguished by a relatively low toxicity and especially by a good gastro-intestinal tolerance, as can be demonstrated with the aid of standard tests.

The novel compounds are useful as antiphlogistic agents, for example for the treatment of rheumatic and arthritic diseases and other diseases associated with inflammation, or as analgesics, for example for the treatment of conditions of pain.

Moreover, the novel compounds of the present invention are suitable as UV absorbers for cosmetic purposes, for example as a constituent of sun-ray filter creams, since they absorb the harmful reddening rays of 290–300 mµ whilst they transmit the desired browning rays of more than 315 mµ.

The diphenylamine-2-acetic acids on which the novel aminoacid amide compounds or peptide amide compounds of the formula I are based are known; they also display antiphlogistic and analgesic actions. Compared with these acids, the novel compounds of the formula I have analogous antiphlogistic actions and somewhat lesser analgesic actions; however, they are distinctly less toxic and better tolerated. Simple amides of the said diphenylamine-2-acetic acids are also known; compared with these, the novel compounds of the formula I, especially those in which at least the aminoacid corresponding to the radical of the formula —N(R$_7$)—R$_5$(R$_6$)—C(=O)— has the D-configuration, have a substantially stronger antiphlogistic action and, moreover, a better therapeutic index.

The invention relates especially to compounds of the formula I in which R$_1$, R$_2$, R$_3$ and R$_4$ are as defined above, R$_5$ is lower alkylene or lower alkylidene, which contain the group R$_6$ and are substituted or unsubstituted, substituents which may be present being hydroxyl, lower alkoxy, mercapto, lower alkylthio, carbamoyl-lower alkoxycarbonyl, carbamoyl, amino, guanidino, phenyl which is unsubstituted or substituted by hydroxyl, or imidazolyl, indolyl or S'-substituted dithio, the second sulphur atom in a S'-substituted dithio group containing, as a substituent, the radical of a compound of the formula I which is bonded via the grouping of the formula —R$_5$(R$_6$)— (Ib) and in which R$_1$, R$_2$, R$_3$, R$_4$, R$_5$, R$_6$, R$_7$ and R$_8$ have the preferred meanings defined in the present context, and R$_6$ and R$_7$ are each hydrogen or together are lower alkylene, which is unsubstituted or substituted by hydroxyl, and the group of the formula —C(=O)—R$_8$ (Ia) is carboxyl, lower alkoxycarbonyl or substituted or unsubstituted carbamoyl, substituted carbamoyl being a group of the formula —C(=O)—N(R$_7{}^a$)—R$_5{}^a$,(R$_6{}^a$)—C(=O)—R$_8{}^a$ (Ic) in which R$_5{}^a$, R$_6{}^a$, R$_7{}^a$ and R$_8{}^a$ have the meanings defined for R$_5$, R$_6$, R$_7$ and R$_8$ respectively, and salts, especially pharmaceutically acceptable salts, of such compounds which contain salt-forming groups. In the abovementioned preferred compounds, the aminoacid compounds or peptide compounds corresponding to the radical of the formula —N(R$_7$)—R$_5$(R$_6$)—C(=O)—R$_8$ are, in particular, those for which the information for protein biosynthesis is available in the genetic code, i.e. aminoacids which are present in naturally occurring peptide or protein substances, and such aminoacids can be in the DL-form or also in the D- or L-form, but preferably at least the aminoacid corresponding to the radical of the formula —N(R$_7$)—R$_5$(R$_6$)—C(=O)— has the D-configuration.

The invention relates in particular to compounds of the formula I in which R$_1$ is hydrogen, lower alkyl having not more than 4 carbon atoms, especially methyl, lower alkoxy having not more than 4 carbon atoms, especially methoxy, halogen having an atomic number of not more than 35, in particular chlorine, or trifluoromethyl and R$_2$, R$_3$ and R$_4$ are each hydrogen, lower alkyl having not more than 4 carbon atoms, especially methyl, lower alkoxy having not more than 4 carbon atoms, especially methoxy, or halogen having an atomic number of not more than 35, in particular chlorine, and in which R$_5$ is lower alkylene or lower alkylidene having not more than 7 carbon atoms, which contains the group R$_6$ and is substituted or unsubstituted and can contain, as substituents, hydroxyl, mercapto, lower alkylthio having not more than 4 carbon atoms, especially methylthio, carboxyl, lower alkoxycarbonyl having not more than 4 carbon atoms in the lower alkoxy moiety, for example methoxycarbonyl or ethoxycarbonyl, carbamoyl, amino, guanidino, phenyl, which can contain hydroxyl, for example 4-hydroxyphenyl, imidazolyl, for example 4-imidazolyl, indolyl, for example, 3-indolyl, or S'-substituted dithio, the second sulphur atom in a S'-substituted dithio group containing, as a substituent, the radical of a compound of the formula I which is bonded via the grouping of the formula —R$_5$(R$_6$)— (Ib) and in which R$_1$, R$_2$, R$_3$, R$_4$, R$_5$, R$_6$, R$_7$ and R$_8$ have the preferred meanings defined in the present context, and R$_6$ and R$_7$ are each hydrogen and the group of the formula —C(=O)—R$_8$ (Ia) is carboxyl, lower alkoxycarbonyl having not more than 4 carbon atoms in the lower alkoxy moiety, for example methoxycarbonyl or ethoxycarbonyl, or substituted or unsubstituted carbamoyl, substitued carbamoyl being a group of the formula —C(=O)—N(R$_7{}^a$)—R$_5{}^a$(R$_6{}^a$)—C(=O)—R$_8{}^a$, in which R$_5{}^a$, R$_6{}^a$, R$_7{}^a$ and R$_8{}^a$ have the meanings defined for R$_5$, R$_6$, R$_7$ and R$_8$ respectively, and a radical of the formula —N(R$_7$)—R$_5$(R$_6$)—C(=O)—R$_8$ (Id) preferably consisting of up to three aminoacid radicals, and also salts, especially pharmaceutically acceptable salts, of such compounds which contain salt-forming groups. In the abovementioned preferred compounds, the aminoacid compounds or peptide compounds corresponding to the radical of the formula —N(R$_7$)—R$_5$(R$_6$)—C(=O)—R$_8$ are, in particular, those for which the information of protein biosynthesis is available in the genetic code, i.e. aminoacids which are present in naturally occurring peptide or protein substances, and such aminoacids can be in the DL-form or also in the D- or L-form, but preferably at least the aminoacid corresponding to the radical of the formula —N(R$_7$)—R$_5$(R$_6$)—C(=O)— has the D-configuration.

The invention relates in particular to compounds of the formula

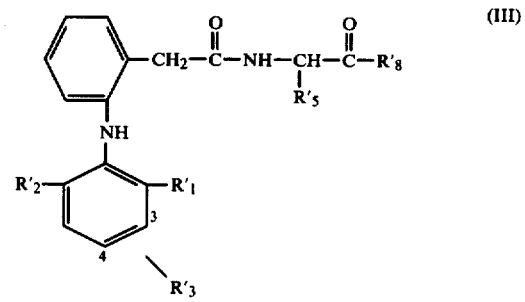

in which R$_1'$ is lower alkyl having not more than 4 carbon atoms, especially methyl, or, in particular, halogen having an atomic number of not more than 35, especially chlorine, R$_2'$ is hydrogen, lower alkyl having not more than 4 carbon atoms, especially methyl, or, in particular, halogen having an atomic number of not more than 35, especially chlorine, and R$_3'$ is hydrogen, with the proviso that R$_3'$ can also be lower alkyl having not more than 4 carbon atoms, especially methyl, in the 3-position if R$_1'$ is one of the said halogen atoms and R$_2'$ is hydrogen, or with the proviso that R$_3'$ can also be halogen having an atomic number of not more than 35, especially chlorine, in the 4-position if R$_1'$ is one of the said halogen atoms and R$_2'$ is hydrogen, and R$_5'$ is hydrogen or lower alkyl having not more than 4 carbon atoms, which is unsubstituted or substituted by hydroxyl, mercapto, lower alkylthio having not more than 4 carbon atoms, especially methylthio, carboxyl, lower alkoxycarbonyl having not more than 4 carbon atoms in the lower alkoxy moiety, for example methoxycarbonyl, or ethoxycarbonyl, carbamoyl, amino, guanidino, phenyl, which can contain hydroxyl, for example 4-hydroxyphenyl, imidazolyl, for example 4-imidazolyl, indolyl, for example, 3-indolyl, or S'-substituted dithio, the second sulphur atom in a S'-substituted dithio group containing, as a substituent, the radical of a compound of the formula II which is bonded via the grouping $R_5'$ and in which $R_1'$, $R_2'$, $R_3'$, $R_5'$ and $R_8'$ have the preferred meanings defined in the present context, for example methyl, ethyl, propyl, isopropyl, n-butyl, isobutyl or sec.-butyl which are unsubstituted or correspondingly substituted, and $R_8'$ is hydroxyl, lower alkoxy having not more than 4 carbon atoms, for example methoxy or ethoxy, or substituted or unsubstituted amino, substituted amino being a radical of the formula $-NH-CH(R_5^{a'})-C(=O)R_8^{a'}$ (IIIa), in which $R_5^{a'}$ and $R_8^{a'}$ have the meanings defined for $R_5'$ and $R_8'$ respectively, and a radical of the formula $-NH-CH(R_5')-C(=O)R_8'$ (IIIb) consisting of one, two or three aminoacid radicals, and also salts, especially pharmaceutically acceptable salts, of such compounds which contain salt-forming groups. In the abovementioned preferred compounds, the aminoacid compounds corresponding to the radical of the formula $-NH-CH(R_5')-C(=O)-R_8'$ (IIIb) are, in particular, those for which the information for protein biosynthesis is available in the genetic code, i.e. aminoacids which are present in naturally occuring peptide or protein substances, and such aminoacids can be in the DL-form or also in the D- or L-form, but at least the aminoacid corresponding to the radical of the formula $-NH-CH(R_5')-C(=O)-$ has the D-configuration.

The invention relates especially to compounds of the formula III in which $R_1'$ and $R_2'$ are each chlorine and $R_3'$ is hydrogen, or $R_1'$ is chlorine, $R_2'$ is hydrogen and $R_3'$ is methyl in the 3-position or chlorine in the 4-position, and $R_5'$ is hydrogen or lower alkyl having not more than 4 carbon atoms which is unsubstituted or substituted by hydroxyl, mercapto, carboxyl, lower alkoxycarbonyl having not more than 4 carbon atoms in the lower alkoxy moiety, for example methoxycarbonyl or ethoxycarbonyl, carbamoyl or phenyl, for example methyl, isopropyl, n-butyl, isobutyl, sec.-butyl, hydroxymethyl, 1-hydroxyethyl, mercaptomethyl, carboxymethyl, carboxyethyl, carbamoylmethyl, carbamoylethyl or benzyl, and $R_8'$ is hydroxyl, lower alkoxy, for example methoxy or ethoxy, amino or substituted amino, substituted amino being a radical of the formula $-NH-CH(R_5^{a'})-C(=O)-R_8^{a'}$ (IIIa), in which $R_5^{a'}$ and $R_8^{a'}$ have the meanings defined for $R_5'$ and $R_8'$ respectively, and a radical of the formula $-NH-CH(R_5')-C(=O)-R_8'$ (IIIb) consisting of one, two or three aminoacid, radicals, and also salts, especially pharmaceutically acceptable salts, of such compounds which contain saltforming groups. In the abovementioned preferred compounds, the aminoacid compounds corresponding to the radical of the formula $-NH-CH(R_5')-C(=O)-R_8'$ (IIIb) are, in particular, those for which the information for protein biosynthesis is available in the genetic code, i.e. aminoacids which are present in naturally occurring peptide or protein substances, and such acids can be in the DL-form or also in the D- or L-form, but at least the aminoacid corresponding to the radical of the formula $-NH-CH(R_5')-C(=O)-$ has the D-configuration.

In particular, the invention relates to the novel compounds described in the examples, preferably those in which at least the aminoacid corresponding to the radical of the formula $-N(R_7)-R_5(R_6)-C(=O)$ has the D-configuration.

The novel compounds of the formula I can be prepared by methods known per se.

Thus, they can be obtained by reacting a compound of the formula

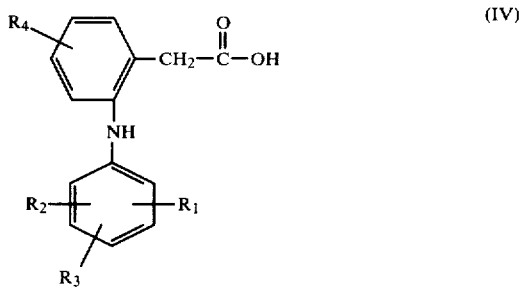

or a reactive derivative thereof, with a compound of the formula

or a derivative thereof, in which compounds any functional groups which may be present can be in a protected form, and, if necessary, converting protected functional groups in compounds obtainable according to the process into the free functional groups, and, if desired, converting a compound of the formula I obtainable according to the process into another compound of the formula I and/or, if desired, converting a salt obtainable according to the process into the free compound or into another salt or converting a free compound obtainable according to the process into a salt and/or, if desired, separating a mixture of isomers obtainable according to the process into the individual isomers.

If desired or necessary, functional groups which may be present in compounds of the formula II and which do not participate in the reaction can temporarily be protected and, at the same time or subsequently, liberated again; suitable protective groups for functional groups are described in detail in the publications mentioned below. Thus, for example, protective groups for carboxyl groups are, for example, esterifying groups, especially lower alkyl, for example methyl, ethyl or tert.-butyl, or phenyl-lower alkyl, for example benzyl or benzhydryl, and for hydroxyl and mercapto groups are, especially, acyl radicals, such as lower alkanoyl radicals, for example acetyl radicals, or aroyl radicals, for example benzoyl radicals, or, in particular, radicals which are derived from carbonic acid compounds, such as benzyloxycarbonyl or lower alkoxycarbonyl, for example ethoxycarbonyl or tert.-butoxycarbonyl, and also benzyl, which is unsubstituted or substituted, for example by nitro, lower alkoxy, such as methoxy, or halogen, for example chlorine, or tetrahydropyranyl radicals.

The reaction of an acid compound of the formula IV with an amine compound of the formula II can be carried out in accordance with the methods customary, for example, in peptide chemistry; publications to be mentioned in this context are, for example, Schröder and Lübke, The Peptides, volumes I and II (Academic Press; 1965), Lübke, Schröder and Kloss, Chemie and Biochemie der Aminosäuren, Peptide und Proteine (Chemistry and Biochemistry of Aminoacids, Peptides and Proteins), volumes I and II (Georg Thieme Verlag, Stuttgart; 1974) and Wünsch, Synthese von Peptiden (Synthesis of Peptides), volume XV/I of Houben-Weyl, Methoden der organischen Chemie (Methods of Organic Chemistry) (George Thieme Verlag, Stuttgart; 1974).

Thus, the novel compounds can be prepared, inter alia, by the so-called anhydride method, by means of which an anhydride of an acid of the formula IV, which may be prepared in situ, is reacted with the amine compound of the formula II. The anhydride method is carried out, in particular, using mixed anhydrides and also symmetrical anhydrides, for example anhydrides with inorganic acids, such as acid halides, especially acid chlorides (which can be obtained, for example, by treating an acid of the formula IV with thionyl chloride, phosphorus pentachloride or oxalyl chloride; acid chloride method), azides (which can be obtained, for example, from an ester of an acid of the formula IV via the corresponding hydrazide and treatment thereof with nitrous acid; azide method), anhydrides with carbonic acid half-derivatives, such as carbonic acid lower alkyl half-esters (which can be obtained, for example, by treating an acid of the formula IV with lower alkyl halogenoformates, such as lower alkyl chloroformates; mixed O-alkylcarbonic acid anhydrides method) or anhydrides with dihalogenated, especially dichlorinated, phosphoric acid, or with phosphorous acid diesters (which can be obtained, for example, by treating an acid of the formula IV with phosphorus oxychloride, chlorophosphorous acid diesters, such as 1,3-butylenedioxychlorophosphite, or diphosphorous acid diesters, such as tetraethyl diphosphite; phosphorus oxychloride method and the known modifications thereof). Furthermore, anhydrides with organic acids, such as mixed carboxylic acid anhydrides (which can be obtained, for example, by treating an acid of the formula IV with phenylacetic acid chloride, pivalic acid chloride or trifluoroacetic acid chloride; mixed carboxylic acid anhydrides method), or symmetrical anhydrides (which can be obtained, for example, by condensation of an acid of the formula IV in the presence of a carbodiimide, such as N,N'-dicyclohexylcarbodiimide, or of 1-diethylamino-propine; symmetrical anhydrides method) can also be used.

A further preferred method for the preparation of the compounds of the formula IV is the activated ester method, according to which an activated ester of an acid of the formula IV, which may be prepared in situ, is reacted with the amine compound of the formula II. The activated esters used are, for example, esters which are unsaturated at the linking carbon of the esterifying radical, for example compounds of the vinyl ester type, such as actual vinyl esters (which can be obtained, for example, by transesterifying an ester of an acid of the formula IV with vinyl acetate; activated vinyl ester method), carbamoylvinyl esters (which can be obtained, for example, by treating an acid of the formula IV with an isoxazolium reagent, for example, 2-ethyl-5-phenyl-isoxazolium 3'-sulphonate; 1,2-oxazolium method or Woodward method) or 1-lower alkoxy-vinyl esters (which can be obtained, for example, by treating the acid of the formula IV with a lower alkoxy-acetylene, for example ethoxyacetylene; ethoxyacetylene method). Furthermore, esters of the amidino type, such as N,N'-disubstituted amidino-esters (which can be obtained, for example, by treating an acid of the formula IV, which, if an acid addition salt, for example the hydrochloride, of the amine component of the formula II is used, can also be employed in the form of a salt, such as an ammonium salt, for example a benzyltrimethylammonium salt, with a suitable N,N'-disubstituted carbodiimide, for example N,N'-dicyclohexyl-carbodiimide; carbodiimide method) or N,N-disubstituted amidino-esters (which can be obtained, for example, by treating an acid of the formula IV with a N,N-disubstituted cyanamide, for example N,N-diethylcyanamide, N,N-diphenylcyanamide or N,N-dibenzylcyanamide; cyanamide method), can also be used.

Preferred activated esters are aryl esters (which can be obtained, for example, by treating an acid of the formula IV with a phenol which is suitably substituted by electron withdrawing substituents, for example 4-nitrophenol, 4-methylsulphonylphenol, 2,4,5-trichlorophenol, 2,3,4,5-pentachlorophenol or 4-phenyldiazophenol, in the presence of a suitable condensing agent, such as 2-ethyl-5-phenyl-isoxazolium 3'-sulphonate, or by transesterification, for example by treating an acid of the formula IV with an aryl ester suitable for transesterification, for example 4-nitrophenyl trifluoroacetate, if necessary in the presence of a suitable transesterification catalyst, for example pyridine; activated aryl ester method).

Further activated esters are, inter alia, cyanomethyl esters (which can be obtained, for example, by treating an acid of the formula IV with chloroacetonitrile in the presence of a base; cyanomethyl ester method), thioesters (which can be obtained, for example, by treating an acid of the formula IV with thiophenols, which are unsubstituted or substituted, for example by nitro, inter alia with the aid of the 1,2-oxazolium or Woodward method; activated thiol-ester method) or amino-esters (which can be obtained, for example, by treating an acid of the formula IV with a N-hydroxyamino compound, for example N-hydroxy-succinimide, N-hydroxy-piperidine, N-hydroxyphthalimide, 8-hydroxy-quinoline or 1-carboxy-2-hydroxy-1,2-dihydro-quinoline, for example by the 1,2-oxazolium or Woodward method; activated N-hydroxy-ester method).

Furthermore, the compounds of the formula I can be prepared by the cyclic amide method, especially by reacting amides of acids of the formula IV with five-membered diazacyclic compounds of aromatic character, such as corresponding imidazolides (which can be obtained, for example, by treating the acid with N,N'-carbonyldiimidazole; imidazolide method) or pyrazolides (which can be obtained, for example, via the acid hydrazide by treatment with acetylacetone; pyrazolide method), with an amine compound of the formula II.

In the context of the preparation of compounds of the formula I in which the radical of the formula —N(R$_7$)—R$_5$(R$_6$)—C(=O)—R$_8$ (Id) is the radical of a corresponding peptide compound of the formula H—N(R$_7$)—R$_5$(R$_6$)—C(=O)—R$_8$ (II), the reaction of an acid starting material of the formula IV with an amine compound of the formula II can also be carried out stepwise, i.e. the aminoacid radicals forming a peptide radical of the formula Id can also be introduced individually or in the form of smaller peptide fragments by the method described above, by, for example, reacting an acid compound of the formula IV, or a reactive derivative thereof, with an aminoacid compound corresponding to the amine compound of the formula II, or with a derivative thereof, or with a smaller peptide compound corresponding to the amine compound of the formula II, or with a derivative thereof, and reacting an amide compound which is thus obtainable, or a reactive derivative thereof, with a further aminoacid compound corresponding to the amine compound of the formula II, or with a derivative thereof, or with a further smaller derivative thereof corresponding to the amine compound of the formula II.

As mentioned, the reaction of an acid compound of the formula IV, or of a reactive derivative thereof, with an amine compound of the formula II, or with a derivative thereof, is carried out in a manner known per se, and, if necessary or desired, is carried out in the presence of a suitable condensing agent, such as a corresponding basic agent, for example an organic base, such as a tri-lower alkylamine, for example triethylamine or diisopropyl-ethyl-amine, or an aromatic or heterocyclic base, for example pyridine, or a mixture of basic agents, usually in the presence of a suitable solvent or solvent mixture and, if necessary, with cooling or warming, for example in a temperature range of from about 0° C. to about 120° C., and also, if necessary, in a closed vessel (if necessary under pressure) and/or in an inert gas atmosphere, for example a nitrogen atmosphere.

The starting materials are known and can be prepared in a manner know per se, if desired in situ. Thus, for example, an amine compound of the formula II can be employed in the form of an acid addition salt, such as a hydrohalide, for example the hydrochloride, and the free amine compound of the formula II can be liberated therefrom in the presence of a suitable basic agent, for example an inorganic metal base or an organic base, such as a suitable amine, for example a tri-lower alkylamine, such as triethylamine or diisopropyl-ethyl-amine.

A further process for the preparation of the compounds of the formula I comprises reducing the carboxyl group X in a compound of the formula

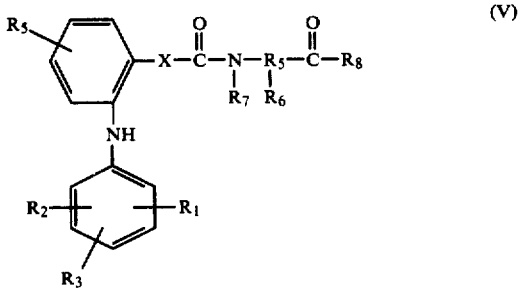

(V)

in which X is a carbonyl group and in which any functional groups which may be present can be in a protected form, to the methylene group and, if necessary or desired, carrying out the additional measures.

Protective groups for functional groups are, in particular, the protective groups mentioned in the publications cited above.

The reduction of the carbonyl group X to the desired methylene group can be carried out in a manner known per se, for example by decomposing the corresponding hydrazone of the starting material of the formula V, in which X is the hydrazonomethylene group of the formula —C(=N—NH$_2$)— (Va), in the presence of a basic agent (Wolff-Kishner method), which hydrazone is formed, preferably in situ, for example by treatment with hydrazine, especially with hydrazine in the form of its hydrate, or, inter alia, can be obtained from the corresponding semicarbazone or azine compounds.

Basic agents which can be used are, inter alia, strong inorganic bases, such as an alkali metal hydroxide, for example potassium hydroxide or sodium hydroxide, or metal alcoholates, such as alkali metal alkanolates, for example sodium methylate or ethylate or potassium methylate or ethylate, or corresponding alcoholates with higher alcohols or polyols. The reaction is carried out in the absence of solvents, but preferably in the presence of suitable solvents, for example high-boiling alcohols, such as polyalkylene glycols, for example diethylene glycol and triethylene glycol (Huang-Minlon modification) or of other suitable solvents, such as dimethylsulphoxide, and, if necessary, with warming (for example up to a temperature of about 220° C.), in a closed vessel (if necessary under pressure) and/or in an inert gas atmosphere, for example a nitrogen atmosphere.

The starting material of the formula V in which X is carbonyl is novel but can be prepared in a manner known per se, for example by reacting a glyoxylic acid compound which corresponds to the starting material of the formula IV and is of the formula

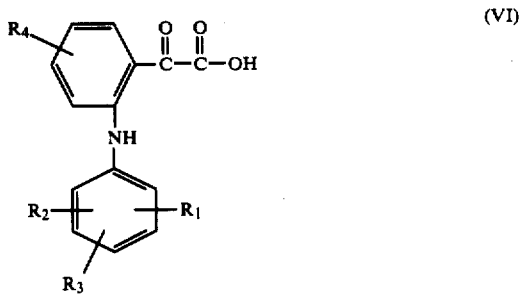

(VI)

or a reactive derivative thereof, with an amine compound of the formula H—N(R$_7$)—R$_5$(R$_6$)—C(=O)—R$_8$ (II), in which any functional groups which may be present can be in a protected form, or with a derivative thereof. The process methods used are those which are customary in peptide chemistry and have been mentioned above.

The novel compounds of the formula I can also be obtained by detaching the amino protective group R$_o$ from a compound of the formula

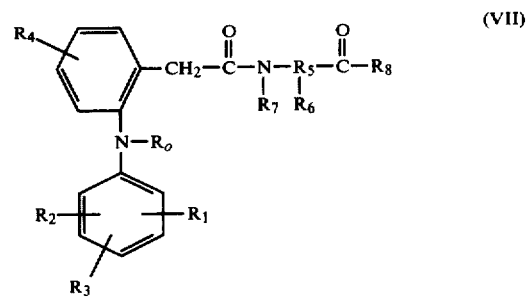

(VII)

in which R$_o$ is an amino protective group and in which any functional groups which may be present can be in a protected form, and replacing it by hydrogen and, if necessary or desired, carrying out the additional process measures.

An amino protective R$_o$ is, in particular, an acyl group, such as acyl of an aliphatic, aromatic or araliphatic carboxylic acid, especially lower alkanoyl, for example acetyl or propionyl, or aroyl, for example benzoyl, or acyl of formic acid or of a carbonic acid half-derivative, for example a carbonic acid half-ester, such as formyl, lower alkoxycarbonyl, for example ethoxycarbonyl or tert.-butoxycarbonyl, or aryl-lower alkoxycarbonyl, for example benzyloxycarbonyl.

An acyl radical used as an amino protective group $R_o$ is detached in a manner know per se, for example by solvolysis, in particular by means of alcoholysis and also by means of hydrolysis. The detaching of an acyl radical $R_o$ by alcoholysis can be carried out, for example, in the presence of a strongly basic agent, at elevated temperature, for example at about 50° C. to about 120° C. The alcohol used is in particular a lower alkanol, for example n-butanol or ethanol, and the strong base used is an alkali metal lower alkanolate, for example a sodium or potassium lower alkanolate, for example sodium n-butylate or ethylate or potassium n-butylate or ethylate, or an alkali metal hydroxide, for example sodium hydroxide or potassium hydroxide.

The starting materials of the formula VII are novel; they can be obtained in a manner known per se, for example by reacting a compound of the formula

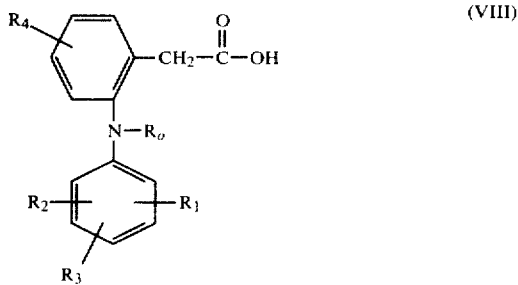

which corresponds to the starting material of the formula IV, or a reactive derivative of the said compound, with an amino compound of the formula H—N(R$_7$)—R$_5$(R$_6$)—C(=O)—R$_8$ (II), in which any functional groups which may be present can be in a protected form, or with a derivative thereof. The process methods used are those which are customary in peptide chemistry and have been mentioned above.

The novel compounds of the formula I can also be obtained by subjecting a compound of the formula

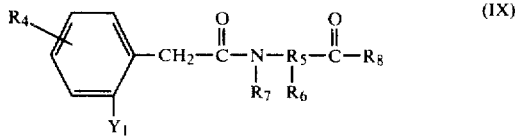

or a salt thereof, to a condensation reaction with a compound of the formula

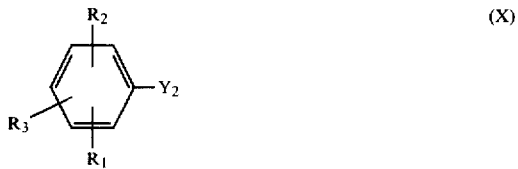

or with a salt thereof, in which compounds one of the radicals $Y_1$ and $Y_2$ is a primary amino group and the other is a leaving group which is replaceable by anilino, and any functional groups which may be present can be in a protected form, and, if necessary or desired, carrying out the additional measures.

The leaving group which is replaceable by anilino is, for example, a halogen atom having an atomic number of 17 to 53, especially iodine.

The condensation reaction of compounds of the formulae IX and X is carried out in a conventional manner, especially in the manner known for analogous nucleophilic substitutions, for example by treatment with copper or with a compound of monovalent copper, for example with copper-I oxide, copper-I chloride, copper-I bromide or copper-I iodide, advantageously in the presence of a basic condensing agent, such as of an alkali metal hydroxide or carbonate or alkaline earth metal hydroxide or carbonate, preferably potassium carbonate, or by using a carboxylic acid of the formula IX, in which $R_8$ is hydroxyl or contains carboxyl, in the form of an alkali metal salt, for example in the form of the sodium or potassium salt. If necessary the reactants are heated, dry or, preferably, in an inert polar organic solvent, such as amyl alcohol, diethylene glycol monomethyl ether or, in particular, dimethylformamide, dimethylacetamide or N-methylpyrrolidone, to about 80° to 200°, and in particular to 100°-180° C., for example to the boiling point.

The compounds of the formula IX to be used as starting materials can be prepared, for example, by subjecting an acid of the formula

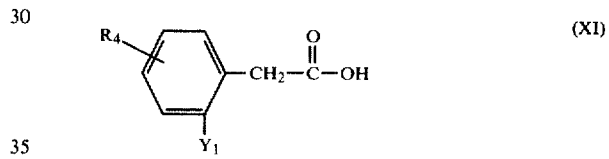

in which an amino group $Y_1$ can be in a protected form, for example in an acetylated form, or a reactive functional derivative thereof, to a condensation reaction with an amino compound of the formula H—N(R$_7$)—R$_5$(R$_6$)—C(=O)—R$_8$ (II), in which functional groups can be in a protected form, or with a derivative thereof, the abovementioned methods customary in peptide chemistry being employed for this reaction. The acids of the formula XI can be obtained, for example, by halogenating the corresponding o-Y$_1$-benzyl alcohol in a conventional manner, for example with thionyl chloride or phosphorus tribromide, converting the o-Y$_1$-benzyl halide, thus obtainable, by means of potassium cyanide into the corresponding o-Y$_1$-phenylacetonitrile and hydrolysing the latter, for example with sulphuric acid or sodium hydroxide solution. If desired, functional derivatives of the acid thus obtainable can be prepared from the acid in a conventional manner.

The starting materials of the formula X are known or can be prepared by methods known per se.

If, in compounds of the formula I obtainable according to the process, functional groups are in a protected form, such groups can be liberated in a manner known per se. Thus, the protected groups can be removed by hydrogenolysis, for example by treatment with hydrogen in the presence of a noble metal catalyst, for example a palladium or platinum catalyst, or by solvolysis, such as hydrolysis, for example acid hydrolysis.

Compounds of the formula I obtainable according to the process can be converted into other compounds of the formula I. Thus, in compounds of the formula I, carboxyl groups of the formula —C(=O)—$R_8$ (Ia), which may be functionally modified, and/or corresponding groups as substituents of the radical $R_5$ can be converted into other groups of the formula Ia or other carboxyl groups, which may be functionally modified. Thus, for example, an esterified carboxyl group can be converted into a free carboxyl group by means of solvolysis, such as hydrolysis or alcoholysis, for example in the presence of a basic agent, such as an alkali metal hydroxide, for example sodium hydroxide or potassium hydroxide, or a suitable esterified carboxyl group, such as benzyloxycarbonyl, can be converted into a free carboxyl group by means of hydrogenolysis, for example by treatment with hydrogen in the presence of a hydrogenation catalyst, such as a palladium catalyst.

Furthermore, a free carboxyl group can be converted to an esterified carboxyl group by one of the conventional esterification processes, such as treatment of the free acid with an alcohol in the presence of an acid, especially a mineral acid, or of a dehydrating agent, such as N,N'-dicyclohexyl-carbodiimide, treatment of a salt, such as a metal salt or ammonium salt, of the free acid with a reactive ester of an alcohol, such as a corresponding halide, treatment of an acid halide with a suitable alcoholate, for example an alkali metal alcoholate, treatment with a suitable diazo compound or any other suitable esterification process, or can be converted into an amidated carboxyl group by one of the conventional amidation processes, for example one of those mentioned above, such as by treatment of an acid halide, for example an acid chloride, with ammonia or an amine or by dehydrating the ammonium salt of an acid. Furthermore, an amidated carboxyl group can also be formed from an esterified carboxyl group, for example by treating the corresponding ester compound with ammonia or an amine.

Furthermore, in a resulting compound of the formula I which contains an esterified carboxyl group, the latter can be converted into another esterified carboxyl group by transesterification, for example by treating an ester with an alcohol in the presence of an acid or basic agent, for example of a corresponding metal alcoholate.

Then, it is possible, in a manner known per se, to convert a compound of the formula I in which the radical of the formula —$R_5(R_6)$— (Ib) contains a mercapto group, by oxidation, for example with oxygen or iodine, into a compound of the formula I in which the group of the formula $R_5(R_6)$— (Ib) contains a S'-substituted dithio group, in which the substituent is the radical of a compound of the formula I bonded via the group of the formula —$R_5(R_6)$— (Ib).

The above reactions are carried out in a conventional manner in the presence or absence of diluents, condensing agents and/or catalytic agents, if necessary at reduced or elevated temperature, in a closed vessel and/or in an inert gas atmosphere.

Depending on the process conditions and starting materials, end products, which can be salt-forming, are obtained in the free form or in the form of their salts and these can be converted into one another or into other salts in a conventional manner. Thus, compounds of the formula I containing a free carboxyl group can be obtained in the form of their salts with bases; these compounds can be converted into a salt, in particular a pharmaceutically acceptable salt, in a conventional manner, for example by reacting the free acid with a corresponding basic agent, such as an alkali metal hydroxide, carbonate, bicarbonate, amide or hydride or an alkaline earth metal hydroxide, carbonate, bicarbonate, amide or hydride or a suitable alkali metal lower alkanolate, or with ammonia or an amine. Free acids of the formula I can be liberated from corresponding salts in a conventional manner, for example by reaction with acid agents. Compounds of the formula I having a basic character can be obtained in the form of their acid addition salts. The latter compounds can be converted into salts by reacting a free basic compound of the formula I with an organic or inorganic acid, especially those which are suitable for forming pharmaceutically acceptable salts. Resulting acid addition salts of basic compounds of the formula I can be converted into the free bases in a manner known per se, for example by treatment with alkaline agents, for example alkali metal hydroxides or basic ion exchangers. Inner salts of compounds of the formula I which contain both an acid salt-forming group and a basic salt-forming group can be obtained, for example, by precipitation at the isoelectric point.

These and other salts can be used to purify the novel compounds, for example by converting the free compounds into their salts, isolating the latter and reconverting these into the free compounds. Because of the close relationship between the novel compounds in the free form and in the form of their salts, what is stated in this specification in respect of the free compounds also applies by analogy to the corresponding salts.

Depending on the choice of starting materials and procedures and depending on the number of asymmetric carbon atoms, the novel compounds can be in the form of optical antipodes or racemates or in the form of mixtures of isomers.

Resulting mixtures of isomers can be separated, on the basis of the physico-chemical differences between the constituents, in a known manner into the two stereoisomers, i.e. the pure isomers, for example by chromatography and/or fractional crystallisation. Advantageously, the more active of the isomers is isolated.

The invention also relates to those embodiments of the process in which a compound obtainable as an intermediate at any stage of the process is used as the starting material and the missing process steps are carried out, or in which a starting material is formed under the reaction conditions or in which a reactant may be employed in the form of its derivatives, such as its salts, and/or in the form of mixtures of isomers or pure isomers.

The starting materials used for carrying out the reactions according to the invention are advantageously those which result in the groups of end products particularly mentioned initially and in particular in the end products specifically described or singled out.

The present invention also relates to pharmaceutical preparations which contain compounds of the formula I or pharmaceutically acceptable salts of such compounds containing salt-forming groups. The pharmaceutical preparations according to the invention are those which are intended for enteral, such as oral or rectal, and parenteral administration to warm-blooded animals and contain the pharmacological active ingredient on its own or together with a pharmaceutically acceptable carrier.

The novel pharmaceutical preparations contain from about 10% to about 95%, and preferably from about 20% to about 90%, of the active ingredient. Pharmaceutical preparations according to the invention are in dosage unit form, such as sugar-coated tablets, tablets, capsules, suppositories or ampoules.

The pharmaceutical preparations of the present invention are prepared in a manner known per se, for example by conventional mixing, granulating, sugar-coating, dissolving or lyophilising methods. Thus, pharmaceutical preparations for oral use can be obtained by combining the active ingredient with solid carriers, granulating a resulting mixture if desired and processing the mixture or granules, after the addition of suitable adjuncts if desired or necessary, to tablets or sugar-coated tablet cores.

Suitable carriers are, in particular, fillers, such as sugars, for example lactose, sucrose, mannitol or sorbitol, cellulose preparations and/or calcium phosphates, for example tricalcium phosphate or calcium hydrogen phosphate, and also binders, such as starch pastes, for example maize, corn, rice or potato starch paste, gelatin, tragacanth, methylcellulose, hydroxypropylmethylcellulose, sodium carboxymethylcellulose and/or polyvinylpyrrolidone, and/or, if desired, disintegrators, such as the above starches and also carboxymethyl starch, cross-linked polyvinylpyrrolidone, agar, alginic acid or a salt thereof, such as sodium alginate. Adjuncts are in particular glidants and lubricants, for example silicic acid, talc, stearic acid or salts thereof, such as magnesium stearate or calcium stearate, and/or polyethylene glycol. Sugar-coated tablet cores are provided with suitable coatings which can be resistant to gastric juices, using, inter alia, concentrated sugar solutions which may contain gum arabic, talc, polyvinylpyrrolidone, polyethylene glycol and/or titanium dioxide, shellack solutions in suitable organic solvents or solvent mixtures or, for the preparation of coatings resistant to gastric juices, solutions of suitable cellulose preparations, such as acetylcellulose phthalate or hydroxypropylmethylcellulose phthalate. Dyes or pigments can be added to the tablets or sugar-coated tablet coatings, for example to identify or indicate different active ingredients.

Further pharmaceutical preparations for oral use are dry-filled capsules made from gelatin and also soft, sealed capsules made from gelatin and a plasticiser, such as glycerin or sorbitol. The dry-filled capsules can contain the active ingredient in the form of granules, for example in admixture with fillers such as lactose, binders such as starches, and/or lubricants such as talc or magnesium stearate, and, if desired, stabilisers. In soft capsules, the active ingredient is preferably dissolved or suspended in suitable liquids, such as fatty oils, paraffin oil or liquid polyethylene glycols, to which stabilisers can also be added.

Preparations suitable for parenteral administration are, in particular, aqueous solutions of an active ingredient in a water-soluble form, for example of a water-soluble salt, and also suspensions of the active ingredient, such as corresponding oily injection suspensions, in which case suitable lipophilic solvents or vehicles, such as fatty oils, for example sesame oil, or synthetic fatty acid esters, for example ethyl oleate or triglycerides, are used, or aqueous injection suspensions which contain substances which increase the viscosity, for example sodium carboxymethylcellulose, sorbitol and/or dextran, and, if desired, also stabilisers.

The invention also comprises the use of the compounds of the formula I, or of pharmaceutically acceptable salts of such compounds containing salt-forming groups, as pharmacologically active substances, especially as anti-phlogistic agents and also as analgesics, preferably in the form of pharmaceutical preparations. The dosage of the active ingredient depends on the species of warm-blooded animal, the body weight and age and on the individual condition, as well as on the mode of administration. On average, the daily dose administered to a warm-blooded animal having a body weight of about 70 kg is from about 50 to about 200 mg and preferably from about 75 to about 150 mg of active ingredient.

The following examples illustrate the present invention without in any way restricting the scope thereof. Temperatures are in degrees Centigrade.

EXAMPLE 1 24.5 ml of triethylamine are added to a solution of 50.5 g of 4-nitrophenyl 2-(2,6-dichlorophenyl-amino)-phenylacetate (melting point 105°–106°) and 21.1 g of the ethyl ester of L-glutamine in 400 ml of chloroform, at room temperature, with stirring. The solution is then stirred at room temperature for five hours and diluted with 1,000 ml of ethyl acetate. The organic solution is washed three times with, in each case, 200 ml of water, twice with, in each ease, 100 ml of 2 N aqueous sodium carbonate solution and with 200 ml of water, dried over magnesium sulphate and evaporated under reduced pressure at 40°. The residue is chromatographed on 1,000 g of silica gel. Fractions 1–7, which are each eluted with 600 ml of methylene chloride, contain starting material. Fractions 8–12, which are each eluted with 600 ml of a 3:1 mixture of methylene chloride and methanol, are combined and evaporated under reduced pressure at 40°. The residue is crystallised from ethanol and this gives the ethyl ester of L-(−)-N-{[2-(2,6-dichlorophenyl-amino)-phenyl]-acetyl}-glutamine; melting point 178°–181°; $[\alpha]_D = -13 \pm 1°$ (c=1.0 in methanol).

The ethyl ester of DL-N-{[2-(2,6-dichlorophenyl-amino)-phenyl]-acetyl}-glutamine can be prepared in an analogous manner and can be saponified to the acid by the method described in Example 2.

EXAMPLE 2

20 ml of 1 N aqueous sodium hydroxide solution are allowed to run dropwise in the course of 30 minutes, at 55°–60°, into a solution of 9.1 g of the ethyl ester of L-(−)-N-{[2-(2,6-dichlorophenyl-amino)-phenyl]-acetyl}-glutamine in 800 ml of ethanol. The solution is then allowed to cool to room temperature and is left to stand for 24 hours. The sodium salt of L-(−)-N-{[2-(2,6-dichlorophenyl-amino)-phenyl]-acetyl}-glutamine, which has crystallised out, is filtered off; melting point 174°–178°; $[\alpha]_D = +5 \pm 1°$ (c=1.0 in water).

EXAMPLE 3

11.0 ml of triethylamine are added to a suspension of 20.9 g of 4-nitrophenyl 2-(2,6-dichlorophenyl-amino)-phenylacetate and 10.8 g of the hydrochloride of the methyl ester of DL-phenylalanine in 125 ml of chloroform, with stirring, and the mixture is stirred at room temperature for 15 hours. The reaction mixture is diluted with 150 ml of ethyl acetate and washed twice with, in each case, 50 ml of 2 N hydrochloric acid, twice with 50 ml of a 2 N aqueous solution of sodium carbonate and twice with 50 ml of water. The organic phase is then dried over magnesium sulphate and evaporated to dryness under reduced pressure. The oily residue is chromatographed on 250 g of silica gel. Fractions 3–16, which are each eluted with 300 ml of methylene chloride, contain the pure methyl ester of DL-N-{[2-(2,6-dichlorophenyl-amino)-phenyl]-acetyl}-phenylalanine; they are combined and evaporated under reduced pressure. The residue is crystallised from ethanol; melting point 148°–150°.

The ethyl ester of N-{[2-(2,6-dichlorophenyl-amino)-phenyl]-acetyl}-glycine, which has a melting point of 161°–162° (after recrystallisation from ethyl acetate), is obtained in an analogous manner using 16.6 g of 4-nitrophenyl 2-(2,6-dichlorophenyl-amino)-phenyl-acetate and 7.6 g of the hydrochloride of the ethyl ester of glycine as the starting materials.

EXAMPLE 4

A solution of 4.4 g of the methyl ester of DL-N-{[2-(2,6-dichlorophenyl-amino)-phenyl]-acetyl}-phenylalanine in 250 ml of methanol is warmed to 50° and 12 ml of a 1 N aqueous solution of sodium hydroxide are added dropwise, with stirring. The solution is stirred at 50° for 2 hours, cooled and evaporated to dryness under reduced pressure. The residue is dissolved in 300 ml of water. The aqueous solution is extracted with 100 ml of diethyl ether and acidified at 0° with 2 N hydrochloric acid. The oil which has separated out is extracted with 100 ml of ethyl acetate. The organic phase is washed with 30 ml of water, dried over magnesium sulphate and concentrated to dryness under reduced pressure. The residue is dissolved in 96 ml of a 0.1 N aqueous solution of sodium hydroxide. The clear aqueous solution (pH 7.0) is lyophilised under a high vacuum and the sodium salt of DL-N-{[2-(2,6-dichlorophenyl-amino)-phenyl]-acetyl}-phenylalanine is obtained in the form of white crystals.

EXAMPLE 5

A solution of 1.55 g of potassium hydroxide in 20 ml of ethanol is added dropwise at room temperature to a suspension of 10.0 g of the ethyl ester of N-{[2-(2,6-dichlorophenyl-amino)-phenyl]-acetyl}-glycine in 100 ml of ethanol. The suspension is then stirred at room temperature for one hour and the solution which is now clear, is evaporated to dryness under reduced pressure. The residue is stirred into 100 ml of water and the solution is washed with 40 ml of diethyl ether and acidified with 2 N hydrochloric acid. The crystals which have separated out are extracted with 500 ml of ethyl acetate. The organic phase is extracted three times with, in each case, 50 ml of a 0.5 N aqueous solution of sodium bicarbonate. The aqueous-alkaline extracts are combined and acidified with 2 N hydrochloric acid. The crystals which have separated out are dissolved in 200 ml of ethyl acetate; the solution is washed with 30 ml of water, dried over magnesium sulphate and concentrated under reduced pressure, whereupon N-{[2-(2,6-dichlorophenyl-amino)-phenyl]-acetyl}-glycine crystallises out; melting point 200°–201°.

EXAMPLE 6

A solution of 25.0 g of 4-nitrophenyl 2-(2,6-dichlorophenyl-amino)-phenyl-acetate and 9.4 g of the hydrochloride of the methyl ester of L-serin in 125 ml of pyridine and 15.5 ml of diisopropyl-ethylamine is stirred for one hour at room temperature and poured onto a mixture of ice and 2 N hydrochloric acid. The crystals which have separated out are extracted with 400 ml of ethyl acetate; the organic phase is washed three times with, in each case, 40 ml of a 1 N aqueous solution of potassium bicarbonate and twice with 50 ml of water, dried over magnesium sulphate and concentrated to dryness under reduced pressure. The residue is crystallised from a mixture of ethyl acetate and petroleum ether; the methyl ester of L-(+)-N-{[2-(2,6-dichlorophenyl-amino)-phenyl]-acetyl}-serine melts at 159°–161°; $[\alpha]_D = +26°\pm 1°$ (c=0.78 in chloroform).

EXAMPLE 7

150 ml of 2 N aqueous sodium hydroxide solution are added to a solution of 15.0 g of the methyl ester of L-(+)-N-{[2-(2,6-dichlorophenyl-amino)-phenyl]-acetyl}-serine in 1,500 ml of ethanol, at room temperature, with stirring. The solution is stirred at room temperature for 16 hours and then evaporated to dryness under reduced pressure. The residue is dissolved in 700 ml of water; the aqueous phase is filtered through a layer of a diatomaceous earth preparation (Hyflo) and the filtrate is washed twice with 100 ml of diethyl ether, cooled to 0° and acidified with concentrated hydrochloric acid. The crystals which have separated out are filtered off, washed thoroughly with water and dried at 50° under 11 mm Hg. L-(+)-N-{[2-(2,6-Dichlorophenyl-amino)-phenyl]-acetyl}-serine melts at 190°–200° with decomposition.

For conversion to the corresponding sodium salt, 14.0 g of the above acid are suspended in 200 ml of water. 36.1 ml of a 1 N aqueous solution of sodium hydroxide are added, with stirring, and the mixture is stirred at room temperature for 30 minutes, during which time a clear solution forms. This solution is then evaporated to dryness under reduced pressure. The residue is dissolved in 300 ml of ethanol; the ethanolic solution is concentrated to about 50 ml under reduced pressure. The residual solution is diluted with 50 ml of diethyl ether and the crystals which have separated out are filtered off. The sodium salt of L-(+)-N-{[2-(2,6-dichlorophenyl-amino)-phenyl]-acetyl}-serine, which is thus obtainable, melts at 175°–190° (with decomposition); $[\alpha]_D = +11°\pm 1°$ (c=1.18 in water).

EXAMPLE 8

12.4 ml of diisopropyl-ethylamine are added to a solution of 20.0 g of 4-nitrophenyl 2-(2,6-dichlorophenyl-amino)-phenyl-acetate and 9.47 g of the hydrochloride of dimethyl L-aspartate in 100 ml of pyridine and the mixture is stirred for 2½ hours at room temperature. The mixture is then poured out onto a mixture of 2 N hydrochloric acid and ice. The oil which has separated out is extracted with 400 ml of chloroform; the chloroform solution is washed with 100 ml of 2 N hydrochloric acid, three times with, in each case, 40 ml of a 2 N aqueous solution of sodium carbonate and with 50 ml of water, dried over magnesium sulphate and concentrated to dryness under reduced pressure. The oily residue is dissolved in ethyl acetate. After adding diethyl ether, dimethyl L-(+)-N-{[2-(2,6-dichlorophenyl-amino)-phenyl]-acetyl}-aspartate crystallises out. The product is filtered off and the white crystals are dried under reduced pressure; melting point 135°–136°; $[\alpha]_D = +58°\pm 1°$ (c=1.07 in chloroform).

EXAMPLE 9

150 ml of a 2 N aqueous solution of sodium hydroxide are added to a solution of 12.0 g of dimethyl L-(+)-N-{[2-(2,6-dichlorophenyl-amino)-phenyl]-acetyl}-aspartate in 3,000 ml of ethanol and the mixture is stirred for 15 hours at room temperature. The resulting white suspension is evaporated to dryness under reduced pressure at room temperature. The residue is dissolved in 500 ml of water and the aqueous solution is acidified with concentrated hydrochloric acid. The crystals which have separated out are filtered off, washed with water and dried under 0.01 mm Hg. L-(+)-N-{[2-(2,6-Dichlorophenyl-amino)-phenyl]-acetyl}-aspartic acid melts at 169°–171°; $[\alpha]_D = -21 \pm 1°$ (c=0.54 in ethanol).

In order to prepare the sodium salt, 10.7 g of the above acid are dissolved in 250 ml of ethanol. 26 ml of a 1 N aqueus solution of sodium hydroxide are added dropwise to the solution and white crystals precipitate out. The suspension is stirred for 30 minutes at room temperature and filtered. The filter residue is washed with a little cold ethanol and dried under 0.1 mm Hg. The monosodium salt of L-(+)-N-{[2-(2,6-dichlorophenyl-amino)-phenyl]-acetyl}-aspartic acid melts at 150°–152° (with decomposition); $[\alpha]_D = +45 \pm 1°$ (c=1.03 in water).

EXAMPLE 10

27.0 ml of diisopropyl-ethylamine are added to a solution of 33.4 g of 4-nitrophenyl 2-(2,6-dichlorophenyl-amino)-phenyl-acetate and 16.96 g of the hydrochloride of dimethyl D-glutamate in 320 ml of chloroform and the mixture is stirred for 15 hours at room temperature. The solution is then washed twice with, in each case, 50 ml of 2 N hydrochloric acid, twice with, in each case, 50 ml of a 2 N aqueous solution of sodium carbonate and with 50 ml of water, dried over magnesium sulphate and evaporated to dryness under reduced pressure. The residue is ground with 50 ml of cold diethyl ether and the crystals formed are filtered off. These are recrystallised from a mixture of ethyl acetae and methylene chloride. Dimethyl D-(−)-N-{[2-(2,6-dichlorophenyl-amino)-phenyl]-acetyl}-glutamate melts at 118°–120°; $[\alpha]_D = -17 \pm 1°$ (c=0.53 in chloroform).

Dibenzyl L-(+)-N-{[2-(2,6-dichlorophenyl-amino)-phenyl]-acetyl}-glutamate, which has a melting point of 74°–76° after recrystallisation from diethyl ether and an $[\alpha]_D = +4° \pm 1°$ (c=0.53 in chloroform), is obtained in an analogous manner using 4.17 g of 4-nitrophenyl 2-(2,6-dichlorophenyl-amino)-phenyl-acetate and 3.63 g of the hydrochloride of dibenzyl L-glutamate as the starting materials.

EXAMPLE 11

A suspension of 10.0 g of dimethyl D-(−)-N-{[2-(2,6-dichlorophenyl-amino)-phenyl]-acetyl}-glutamate in 1,000 ml of ethanol is stirred at room temperature for 20 minutes, during which time a solution forms. 125 ml of a 2 N aqueous solution of sodium hydroxide are then added dropwise at room temperature, with stirring, and the solution is left to stand for 15 hours at room temperature and concentrated to dryness under reduced pressure at 20°. The oily residue is dissolved in 500 ml of water and the clear aqueous solution is acidified at 0° with 2 N hydrochloric acid. The crystals which have separated out are filtered off, washed with 40 ml of water and dried at room temperature under 0.01 mm Hg; D-(−)-N-{[2-(2,6-Dichlorophenyl-amino)-phenyl]-acetyl}-glutamic acid melts at 95°–137° (with long sintering); $[\alpha]_D = -30 \pm 1°$ (c=0.50 in ethanol).

In order to prepare the monosodium salt of the above acid, 8.43 g of D-(−)-N-{[2-(2,6-dichlorophenyl-amino)-phenyl]-acetyl}-glutamic acid are dissolved in 150 ml of ethanol and 19.82 ml of a 1 N aqueous solution of sodium hydroxide are added dropwise to the solution, with stirring. After stirring for 10 minutes, the sodium salt crystallises out from the solution. The suspension is filtered; the crystalline filter residue is washed with cold ethanol and dried under reduced pressure. The monosodium salt of D-(−)-N-{[2-(2,6-dichlorophenyl-amino)-phenyl]-acetyl}-glutamic acid melts at 170°–185° (with stirring); $[\alpha]_D = -43 \pm 1°$ (c=0.97 in water).

EXAMPLE 12

A solution of 14.0 g of dibenzyl L-(+)-N-{[2-(2,6-dichlorophenyl-amino)-phenyl]-acetyl}-glutamate in 300 ml of ethyl acetate is hydrogenated in the presence of 1.4 g of palladium-on-charcoal catalyst (5% strength) at 10°–15° for three hours. The catalyst is filtered off and the filtrate is concentrated to a volume of about 30 ml at 25° under reduced pressure. After adding 150 ml of diethyl ether, L-(+)-N-{[2-(2,6-dichlorophenyl-amino)-phenyl]-acetyl}-glutamic acid crystallises out. The crystals are filtered off and dried at 25° under 0.1 mm Hg; melting point 138°–141°; $[\alpha]_D = +29 \pm 1°$ (c=0.61 in ethanol).

The monosodium salt of the above acid can be prepared by adding 16.57 ml of a 1 N aqueous solution of sodium hydroxide dropwise to a solution of 8.5 g of L-(+)-N-{[2-(2,6-dichlorophenyl-amino)-phenyl]-acetyl}-glutamic acid in 100 ml of ethanol, with stirring; the resulting suspension is cooled to 0° and filtered. The crystalline monosodium salt of L-(+)-N-{[2-(2,6-dichlorophenyl-amino)-phenyl]-acetyl}-glutamic acid melts at 180°–185°; $[\alpha]_D = +42° + 1°$ (c=1.0 in water).

EXAMPLE 13

1.5 ml of triethylamine are added to a solution of 4.2 g of 4-nitrophenyl 2-(2,6-dichlorophenyl-amino)-phenyl-acetate and 3.6 g of the hydrochloride of the methyl ester of L-leucyl-L-serine in 30 ml of dimethylformamide and the mixture is allowed to react for one hour at room temperature. It is then acidified to pH 5 with 1 N hydrochloric acid and partitioned between chloroform and water. After washing with water, the organic phase is dried and evaporated. The residue is ground with diethyl ether. After recrystallising from a mixture of ethyl acetate and petroleum ether, the methyl ester of N-{[2-(2,6-dichlorophenyl-amino)-phenyl]-acetyl}-L-leucyl-L-serine is obtained as colourless crystals; melting point 216°–218°; $[\alpha]_D = -30°$ (c=0.635 in chloroform).

EXAMPLE 14

1.67 ml of triethylamine are added, under a nitrogen atmosphere, to a mixture of 1.45 g of L-cysteine and 4.17 g of 4-nitrophenyl 2-(2,6-dichlorophenyl-amino)-phenyl-acetate in 40 ml of dimethylacetamide and the mixture is stirred for 4 hours at room temperature. The reaction solution is acidified with 1 N hydrochloric acid and evaporated under reduced pressure to a syrup-like residue and the latter is partitioned between chloroform and water. The organic phase is washed with water; its pH value is adjusted to about 5 with triethylamine and it is dried over sodium sulphate and evaporated. The residue is filtered in chloroform through 300 g of silica gel (Merck). The fast-moving by-products are separated off in this way; L-(+)-N-{[2-(2,6-dichlorophenyl-amino)-phenyl]-acetyl}-cysteine is obtained by elution with a 9:1 mixture of chloroform and ethanol. After crystallisation from a mixture of ethanol and water, the product is obtained in the form of colourless crystals; $[\alpha]_D = +37°$ (c=0.97 in methanol).

EXAMPLE 15

Atmospheric oxidation of a solution of L-(+)-N-{[2-(2,6-dichlorophenyl-amino)-phenyl]-acetyl}-cysteine in ethylene chloride at 30°–40° gives L-(−)-bis-N-{[2-(2,6-dichlorophenyl-amino)-phenyl]-acetyl}-cystine in addition to starting material. Crystallisation from diethyl ether gives the pure compound with a melting point of 178°–181°. $[\alpha]_D = -52°$ (c=0.93 in methanol).

EXAMPLE 16

1.4 ml of triethylamine are added, at room temperature, to a solution of 3.9 g of p-nitrophenyl 2-(2,6-dichlorophenyl-amino)-phenyl-acetate and 2.6 g of the hydrochloride of the γ-tert.-butyl ester of D-alanyl-D-glutamic acid α-amide in 20 ml of N,N-dimethylformamide and the mixture is stirred for 15 hours. It is then evaporated to dryness under reduced pressure, the residue is ground several times with ether and the colourless crystals are filtered off. This crystalline product is ground with 0.2 N hydrochloric acid, filtered off with suction and washed, first with dilute sodium bicarbonate solution and then with water. It is then recrystallised from methanol/water. This gives the γ-tert.-butyl ester of N-{[2-(2,6-dichlorophenyl-amino)-phenyl]-acetyl}-D-alanyl-D-glutamic acid α-amide in the form of colorless crystals with a melting point of 230°–235°; $[\alpha]_D = +10°$ (c=1.0 in chloroform).

EXAMPLE 17

2 ml of triethylamine are added to a solution of 3 g of p-nitrophenyl 2-(2,6-dichlorophenyl-amino)-phenyl-acetate and 3 g of the hydrochloride of the methyl ester of L-β-tert.-butylasparaginyl-L-phenylalanine in 15 ml of chloroform and the mixture is left to stand for 15 hours at room temperature. It is then evaporated to dryness under reduced pressure, the residue is taken up in ether and the undissolved material is filtered off. The ether filtrate is extracted several times by shaking with 10% strength sodium carbonate solution, until the ether phase is no longer yellow in colour, and is then washed with water and the ether phase is dried over sodium sulphate and evaporated to dryness. The crystals thus obtained are filtered in chloroform through 100 g of silica gel, in order to remove lipophilic impurities. After evaporating the fractions which contain the desired substance and have been determined by thin layer chromatography ($R_f$ about 0.5 in chloroform), identified in UV light and by spraying with sulphuric acid and warming), the methyl ester of N-{[2-(2,6-dichlorophenyl-amino)-phenyl]-acetyl}-L-β-tert.-butyl-asparaginyl-L-phenylalanine is obtained in the form of colourless crystals with a melting point of 61°–65°; $[\alpha]_D = +24°$ (c=1.0 in chloroform)

EXAMPLE 18

A mixture of 20.0 g of 4-nitrophenyl 2-(2,6-dichlorophenyl-amino)-phenyl-acetate and 9.47 g of the hydrochloride of dimethyl D-aspartate in 9.4 ml of diisopropyl-ethylamine and 100 ml of pyridine is stirred for 1½ hours at room temperature. The resulting yellow solution is poured onto ice, with stirring, and the pH of the suspension is adjusted to 6.0 with 2 N hydrochloric acid. The oil which has separated out is extracted with 200 ml of chloroform. The chloroform solution is washed with 20 ml of 2 N hydrochloric acid, twice with, in each case, 20 ml of water, twice with, in each case, 200 ml of 2 N sodium carbonate solution and with 50 ml of water. The organic phase is then dried over magnesium sulphate and evaporated to dryness under reduced pressure. The residue is crystallised from a mixture of ethyl acetate and ether. Dimethyl D-(−)-N-{[2-(2,6-dichlorophenyl-amino)-phenyl]-acetyl}-aspartate melts at 134°–136°; $[\alpha]_D = -60° \pm 1°$ (c=0.5 in chloroform).

The following compounds are obtained in an analogous manner: the methyl ester of D-(−)-N{[2-(2,6-dichlorophenyl-amino)-phenyl]-acetyl}-serine; melting point 161°–163° after recrystallisation from ethyl acetate; $[\alpha]_D = -25° \pm 1°$ (c=1.0 in chloroform), using 4.17 g of 4-nitrophenyl 2-(2,6-dichlorophenyl-amino)-phenyl-acetate and 1.55 g of the hydrochloride of the methyl ester of D-serine as the starting materials and the methyl ester of D-(−)-N-{[2-(2,6-dichlorophenyl-amino)-phenyl]-acetyl}-methionine; melting point 135°–137° after recrystallisation from ether/petroleum ether; $[\alpha]_D = -39° \pm 1°$ (c=1.0 in chloroform), using 4.17 g of 4-nitrophenyl 2-(2,6-dichlorophenyl-amino)-phenyl-acetate and 2.0 g of the methyl ester of D-methionine as the starting materials.

EXAMPLE 19

250 ml of 2 N sodium hydroxide solution and 50 ml of water are added to a solution of 10.7 g of dimethyl D-(−)-N-{[2-(2,6-dichlorophenyl-amino)-phenyl]-acetyl}-aspartate in 3 l of ethanol. The mixture is stirred at room temperature for 20 hours and then concentrated to dryness under reduced pressure at 20°–25°. The residue is dissolved in 400 ml of water. The clear, bluish solution is extracted with 50 ml of ether and acidified at 0° with concentrated hydrochloric acid. The oil which has separated out crystallises on leaving to stand. The crystals are filtered off, washed with water and dried over phosphorus pentoxide at room temperature under 0.1 mm Hg. D-(−)-N-{[2-(2,6-Dichlorophenyl-amino)-phenyl]-acetyl}-aspartic acid melts at 170°–176°. $[\alpha]_D = -23° \pm 1°$ C. (c=0.5 in ethanol).

In order to prepare the sodium salt, 9.2 g of the above acid are dissolved in 100 ml of ethanol. 22.3 ml of N sodium hydroxide solution are added dropwise to the solution at 0°–5°, with stirring. After the dropwise addition is complete (20 minutes), the crystals which have separated out are filtered off, washed with 50 ml of ether and dried over phosphorus pentoxide for 20 hours at room temperature under 0.1 mm Hg. The monohydrate of the sodium salt of D-(−)-N-{[2-(2,6-dichlorophenyl-amino)-phenyl]-acetyl}-aspartic acid melts at 153°–155°. $[\alpha]_D = -46° \pm 1°$ (c=1.0 in water).

D-(−)-N-{[2-(2,6-Dichlorophenyl-amino)-phenyl]-acetyl}methionine is obtained in an analogous manner; melting point 146°–152°.

EXAMPLE 20

1.47 g of D-glutamic acid are added to a solution of 4.17 g of 4-nitrophenyl 2-(2,6-dichlorophenyl-amino)-phenylacetate in 50 ml of pyridine, at room temperature, with stirring. A mixture of 50 ml of pyridine and 1.7 ml of diisopropylethylamine is then added dropwise. The mixture is stirred for 20 hours at room temperature and poured onto ice. The suspension is acidified with concentrated hydrochloric acid and the oil which has separated out is extracted three times with, in each case, 50 ml of ethyl acetate. The combined organic extracts are extracted four times, at 5°, with, in each case, 80 ml of 2 N sodium carbonate solution. The combined sodium carbonate solutions are acidified at 0° with concentrated hydrochloric acid. The resulting suspension is extracted twice with, in each case, 60 ml of ethyl acetate. These two extracts are combined, dried over magnesium sulphate and concentrated to dryness under reduced pressure. The residue, which consists of yellowish crystals, is chromatographed on silica gel. First runnings are initially eluted with ether and the main fraction is eluted with methanol. The methanolic eluates are combined and evaporated to dryness under reduced pressure. The residue is dissolved in 10 ml of 2 N sodium carbonate solution and the solution is acidified with 2 N hydrochloric acid and extracted with ethyl acetate. The organic phase is dried over magnesium sulphate and evaporated to dryness under reduced pressure. D-(−)-N-{[2-(2,6-Dichlorophenyl-amino)-phenyl]-acetyl}-glutamic acid, which is in the form of yellowish crystals, melts at 95°–137° with decomposition. $[\alpha]_D = -30 \pm 1°$ (c=0.5 in ethanol).

EXAMPLE 21

The following compounds can be obtained in a manner analogous to that described in Examples 1–15:

The methyl ester of L-$N^\alpha$-{[2-(2,6-dichlorophenyl-amino)-phenyl]-acetyl}-lysine, which can be obtained by treating 4-nitrophenyl 2-(2,6-dichlorophenyl-amino)-phenyl-acetate with the hydrochloride of the methyl ester of L-N$\epsilon$-4-methoxybenzyloxycarbonyl-lysine in the presence of a suitable base, for example diisopropyl-ethylamine, and detaching the 4-methoxybenzyloxycarbonyl group by hydrogenolysis with hydrogen in the presence of a palladium catalyst;

L-$N^\alpha$-{[2-(2,6-dichlorophenyl-amino)-phenyl]-acetyl}-lysine and the sodium salt thereof, which can be obtained by solvolysis of the methyl ester of L-$N^\alpha$-{[2-(2,6-dichlorophenylamino)-phenyl]-acetyl}-lysine with an aqueous or alcoholic solution of an alkali metal hydroxide, for example sodium hydroxide; the free acid can be obtained from an alkali metal salt, for example by treatment with an acid, for example hydrochloric acid, and the sodium salt can be obtained from the free acid, for example by treatment with sodium hydroxide;

the methyl ester of L-N$\epsilon$-{[2-(2,6-dichlorophenyl-amino)-phenyl]-acetyl}-lysine, which can be obtained by treating 4-nitrophenyl 2-(2,6-dichlorophenyl-amino)-phenyl-acetate with the hydrochloride of the methyl ester of L-$N^\alpha$-4-methoxybenzyloxycarbonyl-lysine in the presence of a suitable base, for example diisopropyl-ethylamine, and detaching the 4-methoxybenzyloxycarbonyl group by hydrogenolysis with hydrogen in the presence of a palladium catalyst;

L-N$\epsilon$-{[2-(2,6-dichlorophenyl-amino)-phenyl]-acetyl}-lysine and the sodium salt thereof, which can be obtained by solvolysis of the methyl ester of L-N$\epsilon$-{[2-(2,6-dichlorophenyl-amino)-phenyl]-acetyl}-lysine with an aqueous or alcoholic solution of an alkali metal hydroxide, for example sodium hydroxide; the free acid can be obtained from an alkali metal salt, for example by treatment with an acid, for example hydrochloric acid, and the sodium salt can be obtained from the free acid, for example by treatment with sodium hydroxide;

N-{[2-(2,6-dichlorophenyl-amino)-phenyl]-acetyl}-L-asparagyl-L-phenylalanine;

N-{[2-(2,6-dichlorophenyl-amino)-phenyl]-acetyl}-L-alanyl-D-glutamic acid α-amide;

the methyl ester of N-{[2-(2,6-dichlorophenyl-amino)-phenyl]-acetyl}-L-seryl-L-threonine;

the methyl ester of N-{[2-(2,6-dichlorophenyl-amino)-phenyl]-acetyl}-L-isoleucyl-L-glycine; and N-{[2-(2,6-dichlorophenyl-amino)-phenyl]-acetyl}-L-methionyl-L-leucyl-L-phenylalanine.

EXAMPLE 22

Furthermore, the following compounds can be prepared in a manner analogous to that described in Examples 1–21:

D-(−)-N-{[2-(2,6-dichlorophenyl-amino)-phenyl]-acetyl}serine and its sodium salt, D-N-{[2-(2,6-dichlorophenyl-amino)-phenyl]-acetyl}-proline and its sodium salt, D-$N^\alpha$-{[2-(2,6-dichlorophenyl-amino)-phenyl]-acetyl}-lysine and its sodium salt and hydrochloride, D-$N^\alpha$-{[2-(2,6-dichlorophenyl-amino)-phenyl]-acetyl}-arginine and its sodium salt and hydrochloride, D-$N^\alpha$-{[2-(2,6-dichlorophenyl-amino)-phenyl]-acetyl}-glutamine and its sodium salt, the methyl ester of D-N-{[2-(2,6-dichlorophenyl-amino)-phenyl]-acetyl}-phenylglycine and D-N-{[2-(2,6-dichlorophenyl-amino)-phenyl]-acetyl}-phenylglycine and its sodium salt.

EXAMPLE 23

23.9 g of N,N-diisopropyl-ethylamine are added, at room temperature, to a solution of 38.5 g of 4-nitrophenyl 2-(2,6-dichlorophenyl-amino)-phenyl-acetate and 16.8 g of the ethyl ester of D-glutamine in 277 ml of anhydrous pyridine. The solution is stirred for 90 minutes at room temperature, whilst nitrogen is passed through. The solution is then poured into 1,000 ml of ice-water and acidified to pH 2 with concentrated cold hydrochloric acid. The mixture is extracted with 3,000 ml of etyl acetate and the ethyl acetate phase is washed successively with 400 ml of water, twice with, in each case, 300 ml of 2 N sodium carbonate solution and four times with, in each case, 300 ml of water, dried over magnesium sulphate and concentrated to dryness under reduced pressure at 40°. The residue is suspended in 50 ml of diethyl ether and the precipitate is filtered off. The crystals are again suspended in 50 ml of methylene chloride and again filtered off. This gives the ethyl ester of D-(+)-N-{[2-(2,6-dichlorophenyl-amino)-phenyl]-acetyl}-glutamine; melting point 180°–185°; $[\alpha]_D = +11 \pm 1°$ (c=1.08 in methanol). Additional pure product can be obtained from the diethyl ether and methylene chloride mother liquors in the following way: the mother liquors are evaporated to dryness under reduced pressure. The residue is dissolved in 700 ml of methylene chloride. The methylene chloride solution is introduced into a separating column containing 400 g of silica gel. Fractions 1–10, which are each eluted with 300 ml of methylene chloride, contain impurities. Fractions 11–13, which are each eluted with 300 ml of methylene chloride/diethyl ether (3:1), are combined and evaporated to dryness under reduced pressure at 40°. The residue is suspended in 60 ml of ether and the precipitate is filtered off. Additional ethyl ester of D-(+)-N-{[2-(2,6-dichlorophenyl-amino)-phenyl]-acetyl}-glutamine is thus obtained; melting point 181°–185°; $[\alpha]_D = +11 \pm 1°$ (c=1.0 in chloroform).

EXAMPLE 24

The sodium salt of D-(−)-N-{[2-(2,6-dichloro-amino)-phenyl]-acetyl}-glutamine, which has a melting point of 198°–201° (from ethanol) and an $[\alpha]_D = -3 \pm 1°$ (c=1.0 in water), is obtained in a manner analogous to that described in Example 2, using 21.6 g of the ethyl ester of D-(+)-N-{[2-(2,6-dichlorophenyl-amino)-phenyl]-acetyl}-glutamine as the starting material.

EXAMPLE 25

The following compounds are obtained in a manner analogous to that described in Example 6: the methyl ester of D-(−)-N-{[2-(2,6-dichlorophenyl-amino)-phenyl]-acetyl}-serine, which has a melting point of 161°-162° (from ethyl acetate) and an $[\alpha]_D = -25 \pm 1°$ (1.0% strength solution in chloroform), using 41.7 g of 4-nitrophenyl 2-(2,6-dichlorophenyl-amino)-phenylacetate and 15.6 g of the hydrochloride of the methyl ester of D-serine as the starting materials; the methyl ester of D-(−)-{[2-(2,6-dichlorophenyl-amino)-phenyl]-acetyl}-methionine, which has a melting point of 134°-135° (from ethyl acetate) and an $[\alpha]_D = -40 \pm 1°$ (c = 1.0 in chloroform), using 25.0 g of 4-nitrophenyl 2-(2,6-dichlorophenyl-amino)-phenyl-acetate and 12.0 g of the hydrochloride of the methyl ester of D-methionine as the starting materials; and the methyl ester of D-(−)-N-{[2-(2,6-dichlorophenyl-amino)-phenyl]-acetyl}-phenylglycine, which has a melting point of 158°-160° (from ethyl acetate) and an $[\alpha]_D = -109 \pm 1°$ (c = 1.0 in chloroform), using 20.9 g of the 4-nitrophenyl 2-(2,6-dichlorophenyl-amino)-phenyl-acetate and 10.1 g of the hydrochloride of the methyl ester of D-phenylglycine as the starting materials.

EXAMPLE 26

76.5 ml of N sodium hydroxide solution are added to a suspension of 30.4 g of the methyl ester of D-(−)-N-{[2-(2,6-dichlorophenyl-amino)-phenyl]-acetyl}-serine in 1,000 ml of ethanol, with stirring and while passing in nitrogen. The resulting solution is stirred for 19 hours at room temperature. The crystals which have separated out are filtered off and washed with 30 ml of ethanol/diethyl ether (1:1). The filtrate is concentrated to a volume of about 200 ml under reduced pressure at 30° and the crystals which have separated out are filtered off. This crystal fraction consists of the pure sodium salt of D-(−)-N-{[2-(2,6-dichlorophenyl-amino)-phenyl]-acetyl}-serine; melting point 200°-205°; $[\alpha]_D = -17 \pm 1°$ (c = 1.0 in water).

EXAMPLE 27

47.8 ml of N sodium hydroxide solution are added to a suspension of 21.1 g of the methyl ester of D-(−)-N-{[2-(2,6-dichlorophenyl-amino)-phenyl]-acetyl}-methionine in 600 ml of methanol, with stirring and while passing in nitrogen. The suspension is stirred for 20 hours at room temperature and a clear solution forms. This is evaporated under reduced pressure at 30°. The residue is dissolved in 40 ml of methanol. After adding ether, yellow crystals separate out. These are filtered off, washed with 20 ml of ether/ethanol (9:1) and then suspended in 50 ml of diethyl ether/methanol, filtered off and dried for 10 hours at room temperature over phosphorus pentoxide. The sodium salt of D-(−)-N-{[2-(2,6-dichlorophenyl-amino)-phenyl]-acetyl}-methionine (monohydrate) melts at 186°-188°; $[\alpha]_D = -40 \pm 1°$ (c = 1.0 in water).

EXAMPLE 28

In a manner analogous to that described in Example 9, D-(−)-N-{[2-(2,6-dichlorophenyl-amino)-phenyl]-acetyl}-aspartic acid, which has a melting point of 170°-173° and an $[\alpha]_D = -23 \pm 1°$ (c = 0.5 in ethanol), is obtained using 10.7 g of dimethyl D-(−)-N-{[2-(2,6-dichlorophenyl-amino)-phenyl]-acetyl}-aspartate as the starting material, and the monosodium salt of the acid (in the form of the monohydrate), which has a melting point of 151°-143° and an $[\alpha]_D = -46 \pm 1°$ (c = 0.5 in water), is obtained from 9.2 g of the acid.

EXAMPLE 29

In a manner analogous to that described in Example 27, the sodium salt of D-(−)-N-{[2-(2,6-dichlorophenyl-amino)-phenyl]-acetyl}-phenylglycine monohydrate, which has a melting point of 238°-245° (after recrystallisation from methanol/diethyl ether) and an $[\alpha]_D = -8 \pm °$ (c = 1.0 in water), is obtained using 19.65 g of the methyl ester of D-(−)-N-{[2-(2,6-dichlorophenyl-amino)-phenyl]-acetyl}-phenylglycine as the starting material.

EXAMPLE 30

A solution of 2.85 g of p-nitrophenyl 2-(2,6-dichlorophenyl-amino)-phenyl-acetate in 10 ml of pyridine is added to a mixture of 0.75 g of D-penicillamine, 1.29 g of N-ethyldiisopropylamine and 10 ml of pyridine and the mixture is stirred for 20 hours at room temperature. The pyridine is evaporated off under a high vacuum and the residue is dissolved in ethyl acetate. The solution is washed successively with 2 N sodium carbonate solution, N hydrochloric acid and water, dried over sodium sulphate and evaporated. The residue is chromatographed on silica gel using mixtures of toluene and ethyl acetate. The fractions containing the desired product are dissolved in ether, the solution is filtered to give a clear filtrate and the product is precipitated with petroleum ether. This gives the dimer of D-N-{[2-(2,6-dichlorophenylamino)-phenyl]-acetyl}-penicillamine, which has a decomposition point of 160°.

EXAMPLE 31

Tablets containing 25 mg of the sodium salt of L-(−)-N-{[2-(2,6-dichlorophenylamino)-phenyl]-acetyl}-glutamine can be obtained, for example, as follows:

| Composition (for 10,000 tablets) | |
| --- | --- |
| The sodium salt of L—(−)-N—{[2-(2,6-dichlorophenylamino)-phenyl]—acetyl}-glutamine | 250 g |
| Lactose | 460 g |
| Maize starch | 450 g |
| Polyvinylpyrrolidone | 20 g |
| Magnesium stearate | 10 g |
| Colloidal silica | 10 g |
| Water | q.s. |

The sodium salt of L-(−)-N-{[2-(2,6-dichlorophenylamino)-phenyl]-acetyl}-glutamine, the lactose and 450 g of the maize starch are mixed and moistened with an aqueous solution of polyvinylpyrrolidone. The mixture is granulated and dried and the magnesium stearate, the colloidal silica and the remainder of the maize starch are added. The mixture is forced through a sieve, mixed and compressed to tablets weighing 140 mg (diameter: 7 mm).

EXAMPLE 32

Tablets containing 25 mg of the sodium salt of D-(−)-N-{[2-(2,6-dichlorophenyl)-amino-phenyl]-acetyl}-glutamic acid can also be prepared in a manner analogous to that described in Example 31.

EXAMPLE 33

Tablets containing, in each case, 25 mg of another object compound according to any one of Examples 1 to 10 and 12 to 30 can also be prepared in a manner analogous to that described in Example 31.

EXAMPLE 34

Dimethyl L-(+)-N-{[2-(2,6-dichlorophenyl-amino)-phenyl]-acetyl}-glutamate, which has a melting point of 119°-124°, can be prepared in a manner analogous to that described in Example 10, using 4-nitrophenyl 2-(2,6-dichlorophenyl-amino)-phenyl-acetate and dimethyl L-glutamate as the starting materials.

What is claimed is:

1. A phenylacetic acid amide compound of the formula

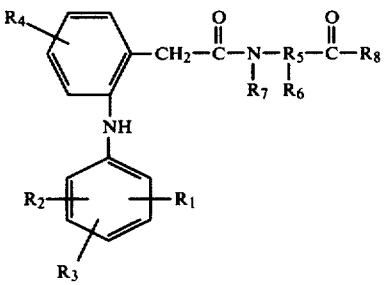

in which each of $R_1$ and $R_2$ is hydrogen, lower alkyl, lower alkoxy, halogen having an atomic number of not more than 35 or trifluoromethyl, each of $R_3$ and $R_4$ is hydrogen, lower alkyl, lower alkoxy or halogen having an atomic number of not more than 35, $R_5$ is lower alkylene or lower alkylidene, $R_6$ is carboxy, lower alkoxycarbonyl, phenyl-lower alkoxycarbonyl or aminocarbonyl, $R_7$ is hydrogen, and the group of the formula —C(=O)—$R_8$ is carboxyl, lower alkoxycarbonyl, or substituted carbamoyl of the formula

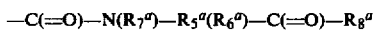

$$-C(=O)-N(R_7^a)-R_5^a(R_6^a)-C(=O)-R_8^a$$

in which $R_5^a$ is lower alkylene or lower alkylidene, $R_6^a$ is phenyl or phenyl substituted by hydroxy, $R_7^a$ is hydrogen and $R_8^a$ is carboxy or lower alkoxycarbonyl, wherein the radical of the formula —$NR_7$—$R_5(R_6)$—CO—$R_8$ has the L-configuration, or a therapeutically acceptable salt thereof.

2. A compound of the formula I according to claim 1, in which $R_1$ is hydrogen, lower alkyl having not more than 4 carbon atoms, lower alkoxy having not more than 4 carbon atoms, halogen having an atomic number of not more than 35, or trifluoromethyl and $R_2$, $R_3$ and $R_4$ are each hydrogen, lower alkyl having not more than 4 carbon atoms, lower alkoxy having not more than 4 carbon atoms or halogen having an atomic number of not more than 35 and in which $R_5$ is lower alkylene or lower alkylidene having not more than 7 carbon atoms, $R_6$ is carboxyl, lower alkoxycarbonyl having not more than 4 carbon atoms in the lower alkoxy moiety, or carbamoyl, and the group of the formula —C(=O)—$R_8$ (Ia) is carboxyl, lower alkoxycarbonyl having not more than 4 carbon atoms in the lower alkoxy moiety.

3. A compound as claimed in claim 1 of the formula

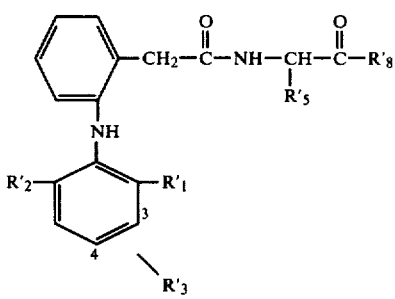

in which $R_1'$ is lower alkyl having not more than 4 carbon atoms or halogen having an atomic number of not more than 35, $R_2'$ is hydrogen, lower alkyl having not more than 4 carbon atoms or halogen having an atomic number of not more than 35 and $R_3'$ is hydrogen, with the proviso that $R_3'$ can also be lower alkyl having not more than 4 carbon atoms in the 3-position, if $R_1'$ is one of the said halogen atoms and $R_2'$ is hydrogen, or with the proviso that $R_3'$ can also be halogen having an atomic number of not more than 35, in the 4-position, if $R_1'$ is one of the said halogen atoms and $R_2'$ is hydrogen, and $R_5'$ is lower alkyl having not more than 4 carbon atoms, which is substituted by carboxyl, lower alkoxycarbonyl having not more than 4 carbon atoms in the lower alkoxy moiety, and $R_8'$ is hydroxyl or lower alkoxy having not more than 4 carbon atoms, or a therapeutically acceptable salt thereof.

4. A compound according to claim 3, in which $R_1'$ and $R_2'$ are each chlorine and $R_3'$ is hydrogen, or $R_1'$ is chlorine, $R_2'$ is hydrogen and $R_3'$ is methyl in the 3-position or chlorine in the 4-position, and $R_5'$ is lower alkyl having not more than 4 carbon atoms which is substituted by carboxyl or lower alkoxycarbonyl having not more than 4 carbon atoms in the lower alkoxy moiety, and $R_8'$ is hydroxyl or lower alkoxy or a therapeutically acceptable salt thereof.

5. A compound according to claim 1 which is L-(+)-N-[[2-(2,6-dichlorophenylamino)-phenyl]-acetyl]-glutamic acid or a therapeutically acceptable salt thereof.

6. A compound according to claim 1 which is dimethyl L-(+)-N-[[2-(2,6-dichlorophenylamino)-phenyl]-acetyl]-aspartate.

7. A compound according to claim 1 which is L-(+)-N-[[2-(2,6-dichlorophenylamino)-phenyl]-acetyl]-aspartic acid or a therapeutically acceptable salt thereof.

8. A compound according to claim 1 which is the methyl ester of N-[[2-(2,6-dichlorophenylamino)-phenyl]-acetyl]-L-beta-tert.butyl-asparaginyl-L-phenylalanine.

9. A compound according to claim 1 which is N-[[2-(2,6-dichlorophenylamino)-phenyl]-acetyl]-L-asparaginyl-L-phenylalanine or a therapeutically acceptable salt thereof.

10. A pharmaceutical preparation containing an antiinflammatory effective amount of a compound as claimed in claim 1 together with conventional pharmaceutical excipients.

* * * * *